United States Patent [19]
Oppenhelm et al.

[11] Patent Number: 5,837,247
[45] Date of Patent: Nov. 17, 1998

[54] CHEMOTACTIC AGENTS FOR T-CELLS

[75] Inventors: Joost J. Oppenhelm, Bethesda; Dennis Michiel, Funkstown; Oleg Chertov, Frederick; Dennis D. Taub, Thurmont, all of Md.; Luoling Xu, London, Canada; Ji Ming Wang; William J. Murphy, both of Frederick, Md.

[73] Assignee: United States of America as represented by the Public Health Service National Institutes of Health, Washington, D.C.

[21] Appl. No.: 491,204

[22] Filed: Jun. 16, 1995

[51] Int. Cl.⁶ .................................................. A61K 39/00
[52] U.S. Cl. .................................... 424/185.1; 424/198.1; 514/12; 530/324
[58] Field of Search ............................. 424/185.1, 198.1; 514/12; 530/324

[56]  References Cited

U.S. PATENT DOCUMENTS

| 4,659,692 | 4/1987 | Lehrer et al. . |
| 5,049,659 | 9/1991 | Cantor et al. . |
| 5,210,027 | 5/1993 | Wilde et al. . |
| 5,242,902 | 9/1993 | Murphy et al. . |
| 5,504,003 | 4/1996 | Li et al. . |

FOREIGN PATENT DOCUMENTS

| 0502718 | 9/1992 | European Pat. Off. . |
| WO 90/13646 | 4/1990 | WIPO . |
| WO 93/19087 | 3/1993 | WIPO . |
| WO 93/24513 | 5/1993 | WIPO . |

OTHER PUBLICATIONS

Territo et al. (1989) J. Clin. Invest. 84(6):2017–20.
Taub et al. (1994) Ther. Immunol. 114:229–246.
Kashkin et al. (1987) Immunologiya 6:37–40.
Zimmer et al., Proc Natl. Acad. Sci USA 89:8215–8219 (1992).

Primary Examiner—Frank C. Eisenschenk
Assistant Examiner—Patrick Nolan
Attorney, Agent, or Firm—Scott A. Brown; Thomas DesRosier

[57]  ABSTRACT

Chemotactic activity of defensins and CAP37 is disclosed. Methods of treatment associated with such activity and compositions for such treatment are also provided.

7 Claims, 5 Drawing Sheets

CHEMOTACTIC AGENTS FOR T-CELLS

This project has been funded at least in part with Federal funds from the Department of Health and Human Services under contract number NO1-CO-74102.

BACKGROUND OF THE INVENTION

Immunologically-induced inflammatory responses are multistep processes involving the production of various chemotactic factors resulting in the orchestrated recruitment of neutrophils, monocytes, T cells and mast cells. The inflammatory α chemokine (1,2), IL-8, a potent chemoattractant and activator of neutrophils, is produced by many cell types including neutrophils (3,4), monocytes (5,6), eosinophils (7) and endothelial cells (8). Two receptors for IL-8 have been cloned and belong to the family of seven transmembrane G protein-coupled receptors (9,10). Signaling through these receptors induces a number of biochemical and biological events including the mobilization of intracellular calcium (11), changes in cellular adhesion (12), respiratory burst (13), degranulation and enzyme release from neutrophils (6,11,14,15).

IL-8 has also been reported to be an in vitro and in vivo chemoattractant for T cells (16). Furthermore, the human T-cell-engrafted SCID mouse has been developed as an in vivo model of chemokine stimulated recruitment and chemotaxis of human T cells and has been used to demonstrate that subcutaneous injection of human IL-8 into these mice causes an initial infiltration of murine neutrophils by 4 h into the site of injection, which is followed by a marked infiltration of human T cells by 72 h.

It would be desirable to determine whether IL-8 produces some of its chemotactic effects indirectly through other mediating factors and, if so, to identify such mediating factors for use as chemotactic agents.

SUMMARY OF THE INVENTION

In preferred embodiments, the present invention provides a method for inducing or stimulating T-cell chemotaxis in a mammalian subject comprising administering to said subject a pharmaceutical composition comprising a therapeutically effective amount of a material selected from the group consisting of a defensin protein, a fragment thereof and a derivative thereof, wherein said material has chemotactic activity for T-cells. Preferably the material is a defensin protein, more preferably a human defensin protein. Preferred defensin proteins include those comprising an amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16 and SEQ ID NO:17. Those comprising the sequence of SEQ ID NO:1 and SEQ ID NO:2 are particularly preferred. The composition for use in such invention may further comprise a pharmaceutically acceptable carrier and/or an additional ingredient which acts on T-cells (such as a cytokine).

In other embodiments, a method is provided for treating a condition which would benefit from induction or stimulation of T-cell chemotaxis in a mammalian subject comprising administering to said subject a pharmaceutical composition comprising a therapeutically effective amount of a material selected from the group consisting of a defensin protein, a fragment thereof and a derivative thereof, wherein said material has chemotactic activity for T-cells.

Methods are also provided for immunizing a subject to an antigen comprising administering to said subject an antigen and a therapeutically effective amount of a material selected from the group consisting of a defensin protein, a fragment thereof and a derivative thereof, wherein said material has chemotactic activity for T-cells. Preferably, the material is administered at the time of administration of said antigen. However, the material can also be administered before or after the antigen.

The present invention also provides methods of inducing an immune response to an antigenic agent (such as a tumor, infectious agent or other diseased tissue) in a subject comprising administering to said subject a therapeutically effective amount of a material selected from the group consisting of a defensin protein, a fragment thereof and a derivative thereof, wherein said material has chemotactic activity for T-cells. Preferably, the material is administered in a manner which attracts T-cells to the site of said antigenic agent.

Methods are also provided for inducing or stimulating T-cell chemotaxis in a mammalian subject comprising administering to said subject a pharmaceutical composition comprising a therapeutically effective amount of a material selected from the group consisting of CAP37, a fragment thereof and a derivative thereof, wherein said material has chemotactic activity for T-cells. Preferably, said material is CAP37 or comprises the amino acid sequence of SEQ ID NO:18. The composition for use in such invention may further comprise a pharmaceutically acceptable carrier and/or an additional ingredient which acts on T-cells (such as a cytokine).

Methods are also provided for treating a condition which would benefit from induction or stimulation of T-cell chemotaxis in a mammalian subject comprising administering to said subject a pharmaceutical composition comprising a therapeutically effective amount of a material selected from the group consisting of CAP37, a fragment thereof and a derivative thereof, wherein said material has chemotactic activity for T-cells.

Methods are also provided for immunizing a subject to an antigen comprising administering to said subject an antigen and a therapeutically effective amount of a material selected from the group consisting of CAP37, a fragment thereof and a derivative thereof, wherein said material has chemotactic activity for T-cells. Preferably, the material is administered at the time of administration of said antigen. However, the material can also be administered before or after the antigen.

The present invention also provides methods of inducing an immune response to an antigenic agent (such as a tumor, infectious agent or other diseased tissue) in a subject comprising administering to said subject a therapeutically effective amount of a material selected from the group consisting of CAP37, a fragment thereof and a derivative thereof, wherein said material has chemotactic activity for T-cells. Preferably, the material is administered in a manner which attracts T-cells to the site of said antigenic agent.

Methods are also disclosed for reducing or inhibiting chemotaxis of T-cells in a subject comprising administering to said subject a therapeutically effective amount of a material selected from the group consisting of an antagonist of a defensin protein and an antagonist of CAP37.

Methods are also provided for reducing or inhibiting an inflammatory or autoimmune condition in a subject comprising administering to said subject a therapeutically effective amount of a material selected from the group consisting of an antagonist of a defensin protein and an antagonist of CAP37.

DETAILED DESCRIPTION OF PREFERRED EMBODIMENTS

Figure 1:
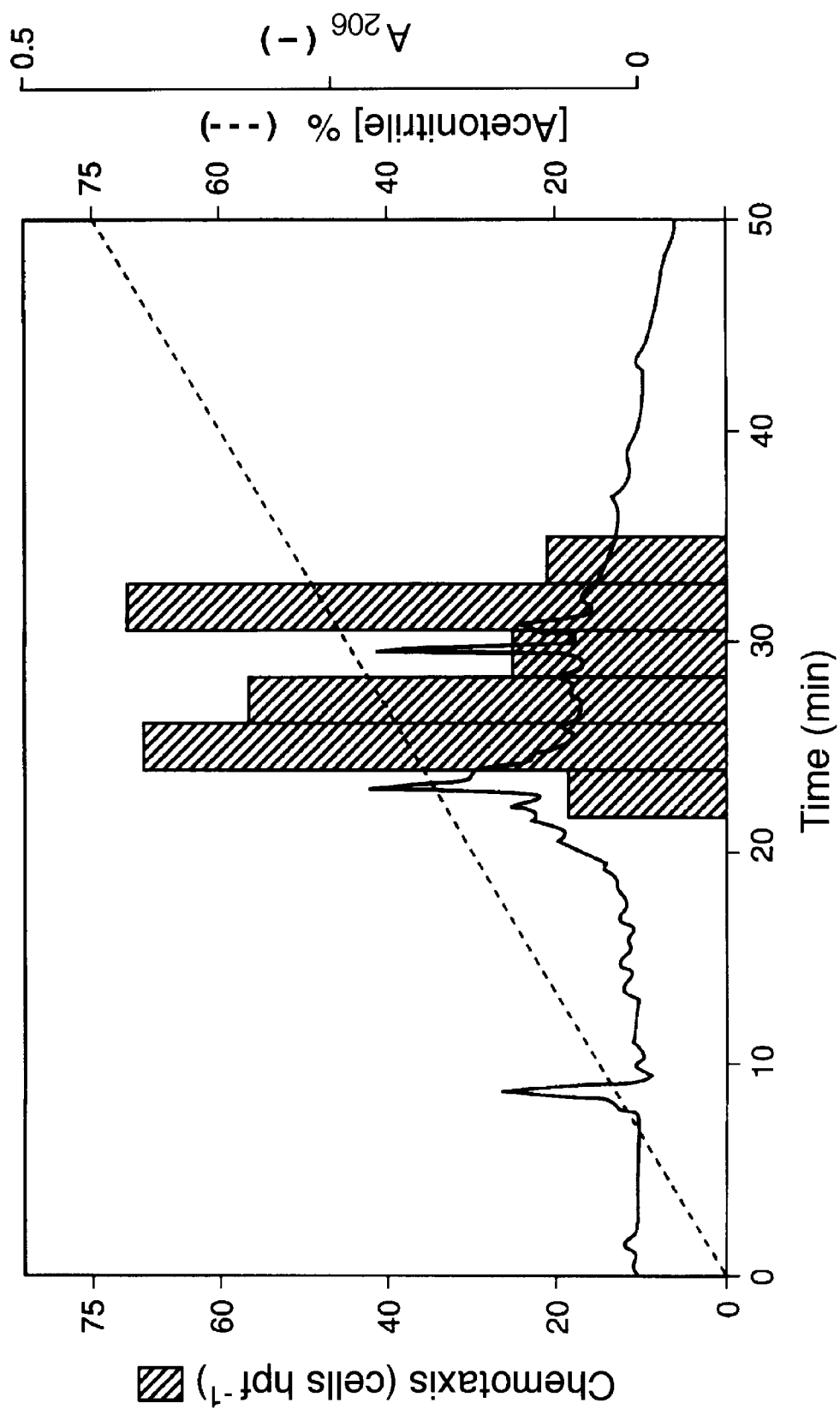
FIG. 1. Partial purification of neutrophil granule-derived T-cell chemotactic factors by reversed phase HPLC. Acid- and salt-extracted proteins from neutrophil granules were loaded on a C18 Radial-Pak HPLC column and eluted with a linear gradient of acetonitrile (---). The absorbance was monitored at 206 nm. Protein-containing fractions were tested for T-cell chemoattractant activity using the microchamber assay.

Reports that IL-8 induces the infiltration of neutrophils followed by T cells into injection sites led applicants to postulate that by stimulation of neutrophil degranulation, IL-8 may cause the release of factors with chemoattractant activity for T lymphocytes. Extracts of human neutrophil granules were chromatographed to isolate and purify T lymphocyte chemoattractant factors. Two major peaks of T-cell chemotactic activity were purified by C18 reversed phase HPLC. The first peak was resolved further by C4 reversed phase HPLC and yielded an active fraction shown by N-terminal amino acid sequence analysis to contain defensin-1 (also known as HNP-1), defensin-2 (also known as HNP-2) and defensin-3 (also known as HNP-3). Purified defensins HNP-1 and HNP-2 were also potent chemoattractants for human T cells, while full-length HNP-3 was relatively inactive. 0.1 to 100 ng/ml defensins were able to stimulate in vitro T-cell chemotaxis. The second peak of T-cell chemoattractant activity was also further purified to homogeneity by C4 reversed phase HPLC and identified by N-terminal sequence analysis as CAP37/azurocidin, a protein with sequence homology to serine proteases. 0.1 to 100 ng/ml defensins and 1.0 to 100 ng/ml CAP37 were able to stimulate in vitro T-cell chemotaxis.

Neutrophil activating factors, i.e. IL-8, PMA/ionomycin and FMLP, each induced the release of CAP37 and defensins from neutrophil granules. Subcutaneous administration of defensins or CAP37/azurocidin into BALB/c mice resulted in a moderate neutrophil and mononuclear cell infiltrate by 4 hr, which was greater by 24 hr at the site of injection. Additionally, subcutaneous injection of defensins into chimeric huPBL-SCID mice, resulted in significant infiltration by human CD3+ cells within 4 hr. These results identify the antimicrobial proteins, CAP37/azurocidin and defensins (including preferably HNP-1 and HNP-2) as potent neutrophil-derived chemoattractants for T cells.

Defensins are a family of small (29–30 amino acids, approx 3.5 kDa) cationic antimicrobial proteins (24) whose structure is stabilized by three conserved disulfide bridges, including one disulfide which cyclizes the protein by linking the carboxy-terminal cysteine to the amino-terminal ultimate (HNP-2) or penultimate (HNP-1, HNP-3) cysteine (29). Indeed the defensins HNP-1, HNP-2 and HNP-3 differ by only a single N-terminal amino acid. Approximately 25–30% of the human azurophilic granule protein consists of defensins. It has been estimated that up to 3–5 ng defensin can be released by each neutrophil. They are believed to be released into the phagocytic vesicle of the neutrophil and into the medium (30) where they contribute to the respiratory burst-independent cytotoxic killing of microbes.

As used herein "defensin" includes all species of defensins, particularly mammalian defensins, including without limitation human, mouse, guinea pig, rabbit and rat defensins. The amino acid sequences of identified defensins are reported in the Sequence Listing as follows:

| human | |
|---|---|
| defensin-1 (HNP-1) | SEQ ID NO:1 |
| defensin-2 (HNP-2) | SEQ ID NO:2 |
| defensin-3 (HNP-3) | SEQ ID NO:3 |
| defensin-4 (HNP-4) | SEQ ID NO:4 |
| defensin-5 (HNP-5) | SEQ ID NO:5 |
| defensin-6 (HNP-6) | SEQ ID NO:6 |
| mouse | |
| Cryptin | SEQ ID NO:7 |
| guinea pig | |
| GPNP | SEQ ID NO:8 |
| rabbit | |
| RNP-1 | SEQ ID NO:9 |
| RNP-2 | SEQ ID NO:10 |
| RNP-3 | SEQ ID NO:11 |
| RNP-3 | SEQ ID NO:12 |
| RNP-4 | SEQ ID NO:13 |
| RNP-5 | SEQ ID NO:14 |
| rat | |
| rNP-2 | SEQ ID NO:15 |
| rNP-2 | SEQ ID NO:16 |
| rNP-3 | SEQ ID NO:17 |

Each of these defensins, in addition to as yet unidentified defensins, can be used in practicing the present invention as long as they possess chemotactic activity for T-cells.

Defensins may be purified from known sources, such as neutrophils, in accordance with known methods. For example, Selsted et al. (41) and Ganz et al. (42) describe purification of defensins from neutrophils. U.S. Pat. No. 5,242,902 also reports methods for purification of defensins. Defensins or fragments, fusions or derivatives thereof can also be synthesized by known protein/peptide synthesis techniques. Defensins or fragments, fusions or derivatives thereof may also be produced by recombinant technology. For example, International Patent Publication WO93/24513 describes methods for doing so. The proteins can be expressed in any suitable cell, including mammalian (such CHO or COS), insect or bacterial cells. In addition to the methods described therein, polynucleotides encoding the desired defensin, fragment, fusion or derivative thereof can be obtained by known screening techniques or can be synthesized.

CAP37/azurocidin, like defensins, was previously identified as a neutrophil granule protein also with antimicrobial activity at micromolar concentrations (32). Structurally, CAP37 belongs to the serine protease superfamily and has 45% sequence identity with human neutrophil elastase, however, due to replacements of crucial amino acids at the active site, CAP37/azurocidin is inactive as a protease (26). Similarly, the antibacterial activity of cathepsin G is independent of its protease activity (33). A peptide consisting of residues 20–44 of CAP37 has been shown to mimic the antibacterial activity of the full length protein (34). It is unlikely that there are any other T-cell chemotactic peptides present that we have not detected in the neutrophil granule extracts, because the defensins and CAP37 are major protein constituents of neutrophil granule and are chemotactic at low (nanomolar) concentrations.

The sequence of CAP37 is reported as SEQ ID NO:18. CAP37 may be produced by purification from known sources in accordance with known methods, including those described in International Patent Publication WO93/19087, Almeida et al. (43), Zimmer et al. (44) and Morgan et al. (45). CAP37, fragments or derivatives thereof can also be synthesized by known protein/peptide synthesis techniques. CAP37 or fragments, fusions or derivatives thereof may also be produced by recombinant technology. For example, International Patent Publication WO93/19087, Almeida et al. (43), Zimmer et al. (44) and Morgan et al. (45) describe methods for doing so. The proteins can be expressed in any suitable cell, including mammalian (such CHO or COS), insect or bacterial cells. In addition to the methods described therein, polynucleotides encoding the desired CAP37, fragment, fusion or derivative thereof can be obtained by known screening techniques or can be synthesized.

Fragments of defensins and CAP37 having chemotactic activity for T-cells can also be used in practicing the present invention. Defensins, CAP37 or fragments thereof can also be incorporated into fusion proteins in accordance with known methods. Such fusion proteins which exhibit chemotactic activity of T-cells can also be used in practicing the invention. Derivatives or modifications (i.e., related proteins or peptides having or mimicking all or a portion of an amino acid sequence) of defensins or CAP37 which exhibit chemotactic activity for T-cells are also useful for practicing the present invention.

A protein or peptide has "chemotactic activity for T-cells," as used herein, if it can stimulate, directly or indirectly, the directed orientation or movement of T-cells. Preferably, the protein or peptide has the ability to directly stimulate directed movement of T-cells. Whether a particular protein or peptide has chemotactic activity for T-cells can be readily determined by employing such protein or peptide in any known assay for T-cell chemotaxis, including without limitation the assay described below.

The cytotoxic effect of defensins occur at micromolar concentrations and is thought to be due to their ability to form numerous transmembrane channels that permeabilize lipid bilayers of microorganisms. Even though their amino acid sequences are virtually identical, HNP-3 does not kill *C. albicans* (31) whereas HNP-1 and HNP-2 have been reported to have this activity. Full-length HNP-3 also lacked T-cell chemotactic activity, suggesting that HNP-1 and HNP-2 may be interacting with receptors or other binding proteins with which full-length HNP-3, with its amino-terminal aspartate residue, cannot interact.

Defensins, HNP-1 and HNP-2, and CAP37 have been reported to chemoattract monocytes (35, 36). However, applicants have repeatedly been unable to detect any monocyte or neutrophil chemotaxis with doses of 1–1000 ng/ml of defensins. In the case of applicants' preparations of natural CAP37/azurocidin and recombinant CAP37, applicants also could not detect significant monocyte chemotaxis (C.I.≦1.5). Perhaps this is based on technical discrepancies in applicants' assays or possibly tissue macrophages express more receptors for CAP37 than do human peripheral monocytes. However, applicants have identified another protein present in the chromatography fractions of the neutrophil granule extracts as having monocyte chemoattractant activity but not T-cell chemotactic activity. This protein migrates very closely to CAP37/azurocidin and may therefore have been a contaminant of CAP37 preparations that attract monocytes. The report that defensins chemoattract human monocytes is based on assays of the leading front of mononuclear cells migrating into a filter (35). It is difficult to identify cells lodging in a filter and this may have led to a misidentification of the migrating mononuclear cell type. Applicants' assay method more readily permits the identification of cells adhering to the underside of polycarbonate filters as T cells. Therefore, defensins are selective in vitro chemoattractants of T cells.

Because defensins account for 25–30% of the neutrophil granule protein content, they may serve as a major source of T-cell chemoattractant whose release is under the control of neutrophil activators such as IL-8. Although serum proteins effectively inactivate the antimicrobial activity of defensins, their in vitro chemotactic activity is not impaired by the presence of 10% FCS. This predicts that defensins or CAP37/azurocidin can deliver a T-lymphocyte activating signal at a distance from the site of acute inflammation where they originate. This prediction was borne out by applicants' experiments showing that BALB/C mice injected subcutaneously with 1.0 µg injections of defensins developed mononuclear as well as neutrophilic infiltrates by 4 hrs. By 24 hrs the number of accumulated neutrophils and mononuclear cells were markedly increased and associated with tissue necrosis. Furthermore, in the case of CAP37/azurocidin considerable numbers of mast cells also infiltrated the local injection sites. The infiltration by neutrophils and mononuclear cells was not predicted by the in vitro assays. It is possible that defensins and CAP37/azurocidin initiate a cascade of proinflammatory signals in vivo resulting in the recruitment of neutrophils and monocytes. The inflammatory response may be a result of the tissue damaging effects of these microbicidal agents, although necrosis became evident only at 24 hrs. In the case of the defensins, immunohistochemical studies revealed that in 4 of the 6 chimeric huPBL-SCID mice, CD3+ human T cells appeared at the injection site already by 4 hrs. However, there are also unstained infiltrating mononuclear cells which are murine macrophages. These macrophages may express more receptors for defensins and CAP37/azurocidin than do circulating monocytes. These observations suggest that these agents are immunomodulators and may have adjuvant activity.

As a result of their chemotactic activity, the defensins, CAP37/azurocidin and active fragments, fusions and derivatives thereof are useful for treatment of conditions which would benefit from stimulation or induction of T-cell chemotaxis, either to a site of desired cell action or away from a site of undesired cell action. For example, there are many situations in which it would be desirable to recruit or mobilize T-cells to a particular site where their presence or action is desired. Such situations include, for example: presentation of an antigen (such as in prophylactic or therapeutic vaccination), where is would be desirable to attract T-cells to the site of inoculation to produce an increased immune response to the antigen (i.e, as an adjuvant); development or direction of an immune response to a tumor, an infectious agent (e.g., virus, bacteria, parasite), diseased tissue or other antigenic agent in the subject's body, where it would be desirable to attract T-cells in order to stimulate an immune response in the area affected by the tumor, infectious agent, diseased tissue or other antigenic agent; and stimulate a change of the balance of T-cell populations at a particular site (such as, for example, stimulating increased infiltration of $T_H2$ cells into the site of a $T_H1$-mediated autoimmune condition). Thus, the chemotactic proteins and peptides can be used to treat, among other conditions, bacterial, viral, fungal and other infections, tumors and other hyperproliferative disorders, immunodeficiencies, diseases susceptible to treatment by administration of a therapeutic vaccine and autoimmune conditions. In other situations, such as for example in autoimmune conditions, it may be desirable to direct or attract T-cells away from a site where they produce an undesired effect. Thus, the agents of the invention can also be used for treatment of conditions caused by the undesirable action of T-cells, including autoimmune conditions. In still other situations, it may be desirable to use the chemotactic agents of the invention to inhibit or reduce chemotaxis of T-cells to an undesired site of action (for example, by administering the agent in order to diminish or eliminate an endogenous in vivo chemotactic gradient (such as, for example, by administering the agent of the invention systemically).

In practicing the methods of treatment of the present invention, the active protein or peptide may be used as a pharmaceutical composition when combined with a pharmaceutically acceptable carrier. Such a composition may contain, in addition to the active protein or peptide and carrier, diluents, fillers, salts, buffers, stabilizers, solubilizers, and other materials well known in the art. The term "pharmaceutically acceptable" means a non-toxic material that does not interfere with the effectiveness of the biological activity of the active ingredient(s). The characteristics of the carrier will depend on the route of administration. The pharmaceutical composition of the invention may also contain other active ingredients, such as, for example, cytokines, lymphokines, or other hematopoietic factors such as M-CSF, GM-CSF, IL-1, IL-2, IL-3, IL-4, IL-5, IL-6, IL-7, IL-8, IL-9, IL-10, IL-11, IL-12, IL-13, IL-14, IL-15, G-CSF, Meg-CSF, stem cell factor, and erythropoietin. Such additional factors and/or agents may be included in the pharmaceutical composition to produce a synergistic effect with the chemotactic protein or peptide, or to minimize side effects.

The pharmaceutical composition of the invention may be in the form of a liposome in which the active ingredient is combined, in addition to other pharmaceutically acceptable carriers, with amphipathic agents such as lipids which exist in aggregated form as micelles, insoluble monolayers, liquid crystals, or lamellar layers in aqueous solution. Suitable lipids for liposomal formulation include, without limitation, monoglycerides, diglycerides, sulfatides, lysolecithin, phospholipids, saponin, bile acids, lipid extracted from whole cells, and the like. Preparation of such liposomal formulations is within the level of skill in the art, as disclosed, for example, in U.S. Pat. No. 4,235,871; U.S. Pat. No. 4,501,728; U.S. Pat. No. 4,837,028; and U.S. Pat. No. 4,737,323, all of which are incorporated herein by reference.

As used herein, the term "therapeutically effective amount" means the total amount of each active component of the pharmaceutical composition or method that is sufficient to show a meaningful patient benefit. When applied to an individual active ingredient, administered alone, the term refers to that ingredient alone. When applied to a combination, the term refers to combined amounts of the active ingredients that result in the therapeutic effect, whether administered in combination, serially or simultaneously.

In practicing the method of treatment or use of the present invention, a therapeutically effective amount of the chemotactic protein or peptide is administered to a mammal having a condition for which T-cell chemotaxis is desired. The chemotactic protein or peptide may be administered in accordance with the method of the invention either alone or in combination with other therapies such as treatments employing cytokines, lymphokines or other hematopoietic factors. When co-administered with one or more cytokines, lymphokines or other hematopoietic factors, the chemotactic protein or peptide may be administered either simultaneously with the cytokine(s), lymphokine(s), other hematopoietic factor(s), thrombolytic or anti-thrombotic factors, or sequentially. If administered sequentially, the attending physician will decide on the appropriate sequence of administering the chemotactic protein or peptide in combination with cytokine(s), lymphokine(s), other hematopoietic factor (s), thrombolytic or anti-thrombotic factors.

Administration of the chemotactic protein or peptide used in the pharmaceutical composition or to practice the method of the present invention can be carried out in a variety of conventional ways, such as oral ingestion, inhalation, cutaneous application, injection at a subcutaneous, intramuscular or intra-organ site, or intravenous administration.

When a therapeutically effective amount of the chemotactic protein or peptide is administered orally, the chemotactic protein or peptide will be in the form of a tablet, capsule, powder, solution or elixir. When administered in tablet form, the pharmaceutical composition of the invention may additionally contain a solid carrier such as a gelatin or an adjuvant. The tablet, capsule, and powder contain from about 5 to 95% of the chemotactic protein or peptide, and preferably from about 25 to 90% of the chemotactic protein or peptide. When administered in liquid form, a liquid carrier such as water, petroleum, oils of animal or plant origin such as peanut oil, mineral oil, soybean oil, or sesame oil, or synthetic oils may be added. The liquid form of the pharmaceutical composition may further contain physiological saline solution, dextrose or other saccharide solution, or glycols such as ethylene glycol, propylene glycol or polyethylene glycol. When administered in liquid form, the pharmaceutical composition contains from about 0.5 to 90% by weight of the chemotactic protein or peptide and preferably from about 1 to 50% of the chemotactic protein or peptide.

When a therapeutically effective amount of the chemotactic protein or peptide is administered by intravenous, cutaneous or subcutaneous injection, the chemotactic protein or peptide will be in the form of a pyrogen-free, parenterally acceptable aqueous solution. The preparation of such parenterally acceptable protein solutions, having due regard to pH, isotonicity, stability, and the like, is within the skill in the art. A preferred pharmaceutical composition for intravenous, cutaneous, or subcutaneous injection should contain, in addition to the chemotactic protein or peptide an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition of the present invention may also contain stabilizers, preservatives, buffers, antioxidants, or other additive known to those of skill in the art.

The amount of the chemotactic protein or peptide in the pharmaceutical composition of the present invention will depend upon the nature and severity of the condition being treated, and on the nature of prior treatments which the patient has undergone. Ultimately, the attending physician will decide the amount of the chemotactic protein or peptide with which to treat each individual patient. Initially, the attending physician will administer low doses of the chemotactic protein or peptide and observe the patient's response. Larger doses of the chemotactic protein or peptide may be administered until the optimal therapeutic effect is obtained for the patient, and at that point the dosage is not increased further. Preferred dosages of the pharmaceutical compositions used to practice the method of the present invention provide about 0.01 $\mu$g to about 50 $\mu$g, preferably about 0.01 $\mu$g to about 10 $\mu$g, more preferably about 0.01 $\mu$g to about 1 $\mu$g, of the chemotactic protein or peptide.

The duration of therapy using the pharmaceutical composition of the present invention will vary, depending on the severity of the disease being treated and the condition and potential idiosyncratic response of each individual patient. Ultimately the attending physician will decide on the appropriate duration of therapy using the pharmaceutical composition of the present invention.

When chemotactic agents of the invention are used in combination with administration of an antigen (e.g., in vaccination), the antigen can be delivered in accordance with known methods. The chemotactic agent can be administered at the time of, before or after administration of the antigen. Simultaneous administration can be made in a single composition containing antigen and chemotactic agents or in separate preparations.

When the chemotactic agents of the invention are used to induce an immune response to an antigenic agent (such as, for example, a tumor, infectious agent or other diseased tissue) in the treated subject, the chemotactic agent can be delivered as described above. Preferably, the agent is administered in a manner which will attract T-cells to the site of the antigenic agent. For example, the chemotactic agent can be injected into or into the region of a tumor in order to promote migration of T-cells to the tumor site. Similarly, the chemotactic agent can also be administered in an area of infection by a virus or bacteria to promote migration of T-cells to the site of infection.

Antagonists of defensins and CAP37/azurocidin (such as, for example, polyclonal or monoclonal anitbodies to these agents, soluble receptors for these agents, or fragments or derivatives of these agents capable of binding to the agents' receptors without inducing some or all of the chemotactic activity induced by the agent in the absence of the antagonist) may be used to counteract the effects of defensins or CAP37/azurocidin in vivo. For example, antagonists can be administered to reduce, inhibit or eliminate an inflammatory or autoimmune condition which is induced, in whole or in part, by the antagonized agent. Methods of producing antibodies to these chemotactic agents are known in the art. Methods of producing antagonistic fragments and derivatives of these agents is also within the skill of the art. Fragments and derivatives can be produced with known molecular biology or synthetic techniques. Antagonists can be tested for competition with the agent to be antagonized in assays for T-cell chemotaxis, wherein functional antagonists can be identified by the reduction or abolition of chemotactic activity.

Other neutrophil- and monocyte-derived serine protease homologues, such as neutrophil elastase (NE) and proteinase 3 (PR3), are also useful for practicing the methods of the present invention.

The following examples are intended to illustrate preferred embodiments of the present invention and should not be interpreted as limiting the claimed invention.

EXAMPLES

Materials and Methods

Reagents. Rabbit anti-human CAP37 antisera was prepared by immunization with purified azurocidin/CAP37 in Freund's adjuvant. Defensins were purified from neutrophils according to the methods of Selsted et al. (41) and Ganz et al. (42).

T-Cell Preparations. Human peripheral blood enriched in mononuclear cells or lymphocytes was obtained from normal donors by leukapheresis (National Institutes of Health Clinical Center, Department of Transfusion Medicine, Bethesda, Md.). The blood was centrifuged through Ficoll-Hypaque at 800×g for 30 min. The mononuclear cells (PBMC) at the interface were washed twice with PBS and centrifuged through an isosmotic Percoll gradient as described to remove monocytes. Human T-cell enrichment columns (R&D Systems, Minneapolis, Minn.) were then used according to the manufacturer's instructions to rapidly purify the T cells using high affinity negative selection. This isolation procedure typically yields greater than 90% $CD3^+$ T cells. The cells were resuspended in chemotaxis medium (RPMI 1640 containing 1% BSA and 25 mM HEPES).

Chemotaxis Assay. T lymphocyte migration was assessed using a 48 well microchemotaxis chamber (Neuro Probe Inc. Cabin John, Md.), as reported (17). 25 $\mu$l of the sample to be tested diluted in chemotaxis medium was placed in the lower compartment and 50 $\mu$l of cell suspension (at $5 \times 10^6$ cells $ml^{-1}$) in the upper compartment. The two compartments were separated by a polycarbonate filter (5 $\mu$m pore size) coated with 10 $\mu$g/ml collagen type IV overnight at 4° C. The apparatus was incubated at 37° C. for 3 h in humidified air with 5% $CO_2$. At the end of the incubation period, the filter was removed, fixed and stained with LeukoStat (Fisher Scientific, Pittsburgh, Pa.). The number of cells that migrate through the filter were counted by light microscopy per high-power fields. The results are expressed as the mean (±SD) value of the migration in triplicate samples and are representative of at least three experiments. The statistical significance of the number of cells migrating in response to stimuli versus control medium was calculated using the Student's T test.

Neutrophil Granule Preparations. Human neutrophils were isolated from granulocyte packs obtained from the Department of Transfusion Medicine, Warren Grant Magnuson Clinical Center, NIH, Bethesda, Md. Neutrophils were isolated by the method of Boyum (18). Briefly, erythrocytes were removed by sedimentation with 1.5% dextran. Mononuclear cells were centrifuged on a Ficoll-Hypaque cushion and the residual erythrocytes were removed by hypotonic lysis. The neutrophils were resuspended in PBS, counted and assessed for viability. Following a wash with PBS, the neutrophils were resuspended in disruption buffer (0.25M sucrose, 10 mM HEPES (pH 7.4) containing 4 mM EGTA). Neutrophils were lysed by nitrogen cavitation and granule fractions were separated on Percoll gradients (19). The cells were equilibrated at 450 p.s.i. for 20 min. in a nitrogen bomb and lysed by dropwise release. Nuclei and cell debris were removed by centrifugation at 600×g for 10 min. The supernatant was layered over 48% Percoll and centrifuged at 29,000 rpm for 26 min. The Percoll gradient was fractionated and the fractions were assessed for granule enzymes and T-cell chemotactic activity. Granule fractions were pooled and recentrifuged at 35,000 rpm for three hours. The granules were recovered as a white flocculent material just above the Percoll pellet. At this point the granules were aliquoted and stored at $-70°$ C. until further use.

Purification of T-cell Chemoattractant Activity. Neutrophil granules (0.5 ml) were lysed by freeze-thawing (three times) in 3 ml of 0.1% TFA containing 2M NaCl. The suspension was centrifuged for 15 min at 800×g. 1 ml of clarified supernatant was applied to a C18-300A reversed phase HPLC cartridge column (8×100 mm, Delta-Pak, Millipore) equilibrated with 0.1% TFA (Buffer A). Absorbed proteins were eluted with a linear gradient of 0–90% Buffer B (0.05% TFA in acetonitrile) over 60 min. at a flowrate of 1 ml min$^{-1}$ (FIG. 1). Absorbance at 206 nm was monitored as a measure of protein concentration. Collected fractions were lyophilized and assayed for chemotactic activity.

Figure 2:
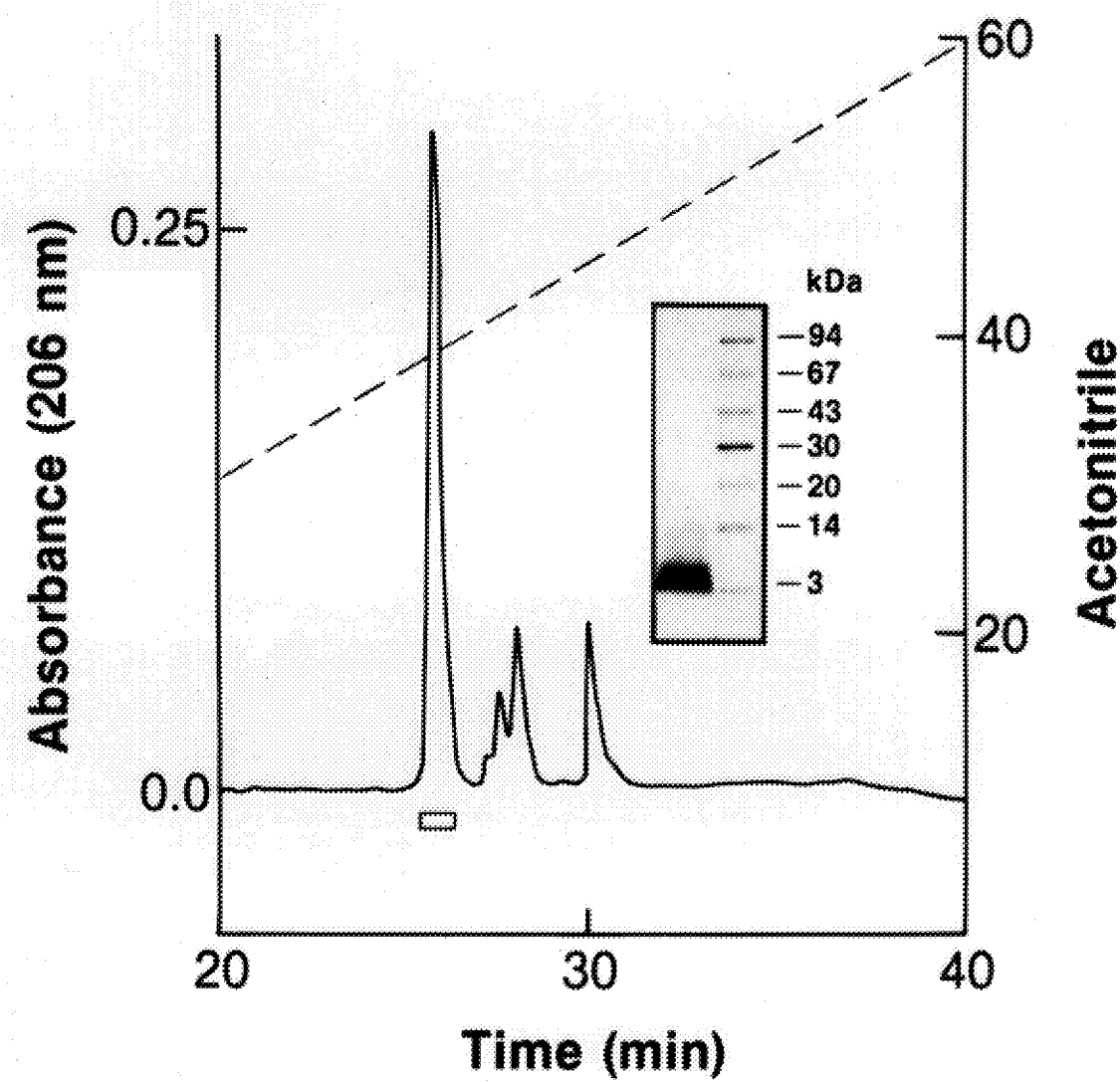
FIG. 2. Purification of defensins by C4 reversed phase chromatography. The first peak of activity from the C18 column was lyophilized, loaded onto a C4 reversed phase HPLC column and eluted with a gradient of acetonitrile (---). Fractions were tested for activity using the microchamber assay. Active fraction, indicated by the open rectangle beneath the absorbance trace, showing one peptide band on gradient (10–20%) Tris-tricine gel with coomassie staining (see insert) was sequenced and identified as HNP-1, HNP-2 and HNP-3.
Figure 3:
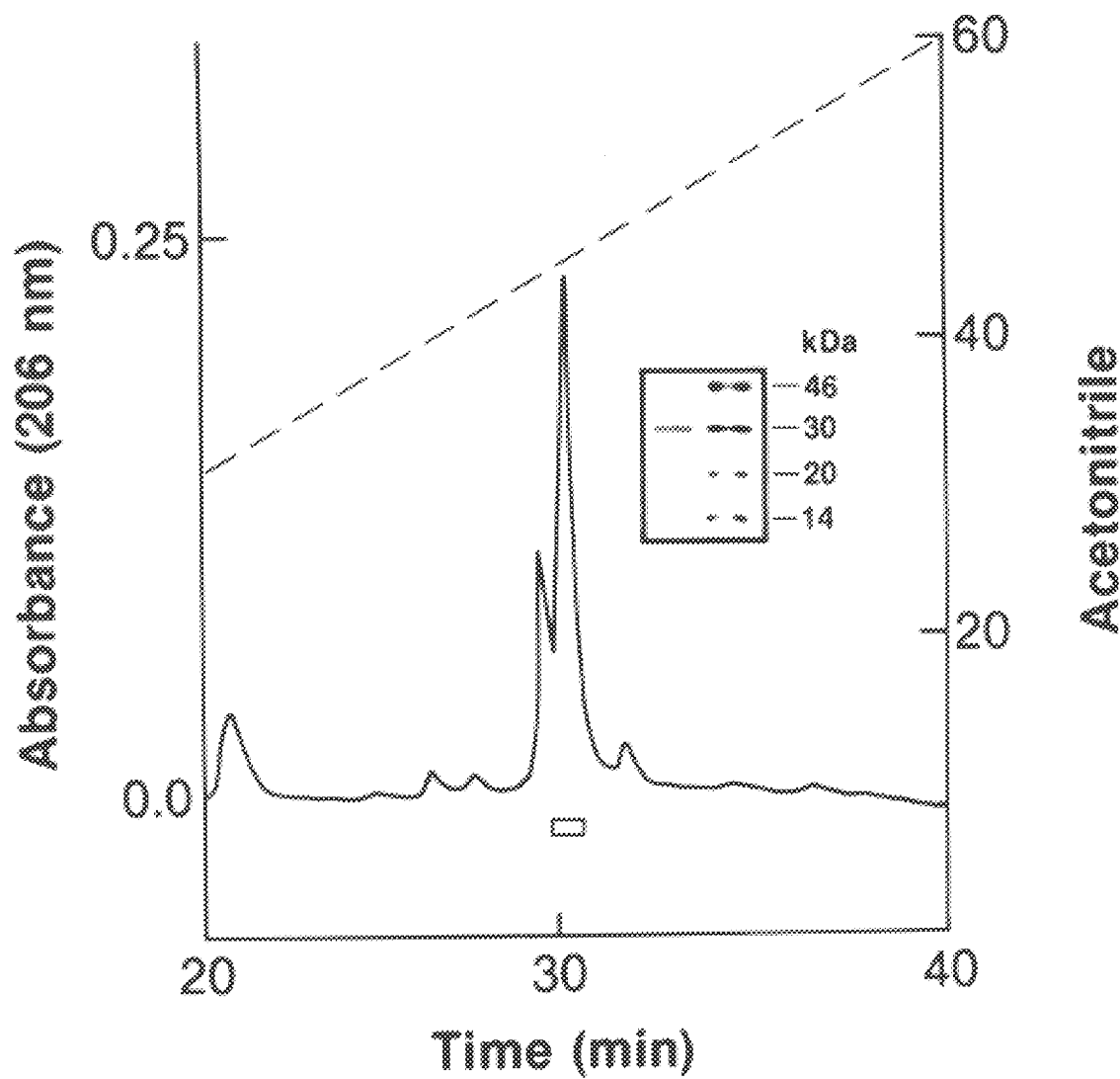
FIG. 3. Purification of CAP37/azurocidin by C4 reversed phase chromatography. The second peak of activity from the C18 column was lyophilized, loaded onto a C4 reversed phase HPLC column and eluted with a gradient of acetonitrile (---). Fractions were tested for activity using the microchamber assay. The active fraction, indicated by the open rectangle and showing one protein band on 15% Tris-glycine SDS-PAGE, was sequenced and identified as CAP37/azurocidin.

Identification of Chemoattractant Proteins. Fractions containing chemoattractant activity were pooled, lyophilized, redissolved in Buffer A and applied to a C4 reversed phase HPLC column (4.6×250 mm, BioRad, RP-304). Proteins were eluted with a linear gradient of 0–90% Buffer B over 60 min. at a flowrate of 0.5 ml min$^{-1}$ (FIGS. 2 and 3). Fractions with activity were analyzed by SDS-PAGE (20) and used for automatic sequence analysis on a Applied Biosystems sequencer model 477A. The presence of cysteine residues was inferred from the absence of detectable amino acid.

Release of Granule Contents. Neutrophils (2×10$^6$ ml$^{-1}$) suspended in AIM-V medium (life Technologies, Grand Island, N.Y.) were incubated at 37° C. in 6-well plates that had been coated with fibronectin or V-CAM. Exocytosis was initiated by addition of the appropriate stimulus and stopped by removal of the supernatant and centrifugation. Elastase, lactoferrin and β-glucosidase were assayed (20,21) and detected to demonstrate that IL-8 was effective in degranulating the neutrophils. Protein in the cell-free media was concentrated using StrataClean resin (Stratagen Cloning Systems, La Jolla, Calif.), separated by SDS-PAGE and Western blotted using a rabbit anti-defensin antisera.

In vivo studies. BALB/C and CB-17 scid/scid (SCID) mice were obtained from the Animal Production Area (NCI-FCRDC, Frederick, Md.). Mice were used at 8–12 wk of age and kept in pathogen free conditions as described (22). SCID mice were treated with anti-ASGM-1 and injected with 1×10$^8$ huPBL i.p. as described (22). Immediately thereafter 0.1 ml PBS containing purified preparations of 1.0 µg defensins, CAP37/azurocidin or control PBS were injected daily×1 subcutaneously into the same injection site. Chromogenic LAL assays for endotoxin contamination in the purified peptides revealed 0.05 EU/20 µg defensins and 0.114 EU/20 µg CAP37/azurocidin. The injection site was examined histologically either at 4 hr after the first or at 24 hr by 4 hr after a second injection. Experiments were performed on three to four mice per group in duplicate. Histological and immunohistochemical examinations were performed as previously described (22).

Results

Identification of Defensins as T-cell Chemoattractants. Human neutrophil granule proteins were extracted by repeated freeze-thawing in a solution of high salt and acid pH. These granule extracts yielded a T-cell chemoattractant activity which was concentrated and partially purified by C18 reversed phase HPLC chromatography. This resulted in two major peaks of chemotactic activity eluting at 37% and 46% acetonitrile (FIG. 1). The proteins with chemotactic activities were further resolved by chromatography on a C4 reversed phase HPLC column. The first peak of activity was purified to apparent homogeneity (FIG. 2), appearing as a single band that migrated with an apparent molecular mass of approx. 3 kDa on Tris-tricine SDS-PAGE (23). N-terminal sequence analysis revealed the presence of three related sequences (Table 1) corresponding to defensin HNP-1 (50% of the material), HNP-2 (30%) and HNP-3 (20%). Detection of only defensin sequences by sequence analysis and the correspondence of amino acid analysis of the preparation with amino acid composition of defensins suggests that the preparation consisted of at least 95% pure defensins.

Figure 4:
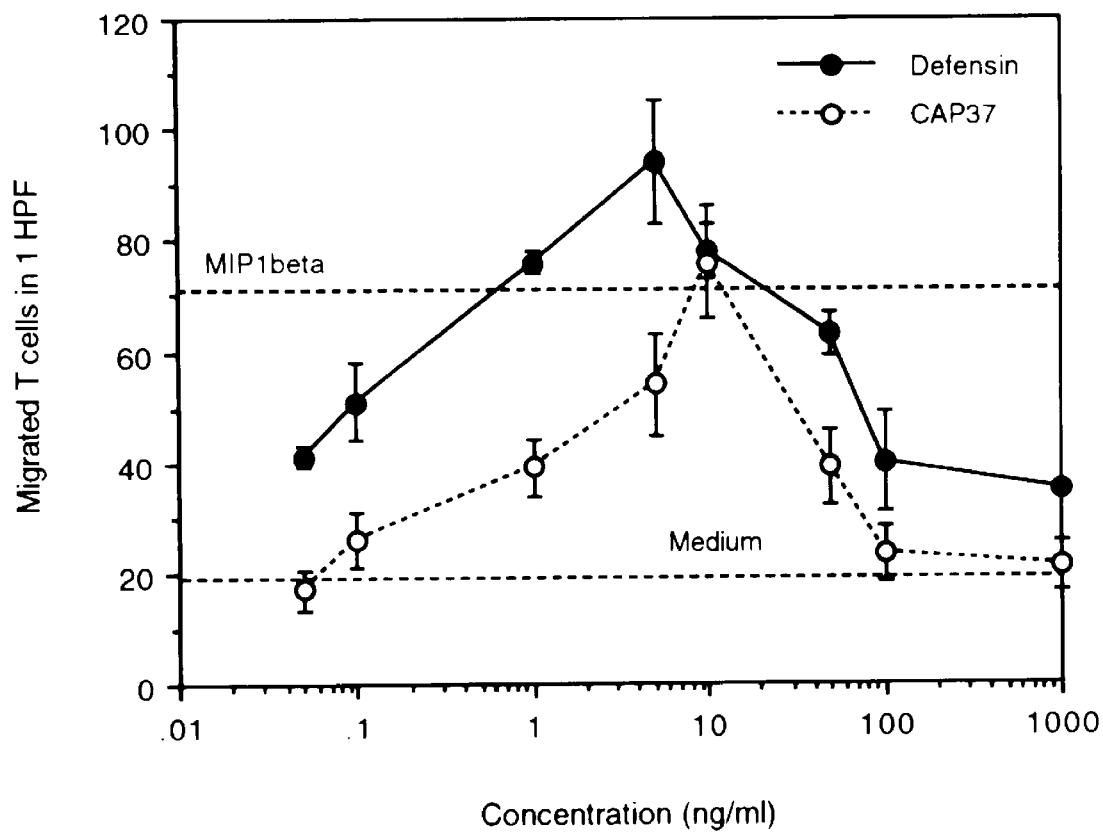
FIG. 4. Purified defensins and CAP37/azurocidin are chemotactic for T cells. C4 purified defensins, (a mixture of HNP-1, HNP-2 and HNP-3) and CAP37/azurocidin were tested at different concentrations for T-cell chemotactic activity. MIP-1b (5 ng/ml) is included as a positive control. The migration was performed using the Boyden chamber assay on collagen-coated filters as described in Materials and Methods. The results in this representative experiment are expressed as the mean number of T cells which have migrated through the filter per high power field.

The T-cell chemotactic activity of homogeneous preparations of neutrophil-derived HNP-1, HNP-2 and HNP-3 were compared to the preparation described above. The dose response to individual HNP-1 and HNP-2 was practically identical to that of the preparation containing a mixture of HNP-1, HNP-2 and HNP-3 (FIG. 4). Checkerboard analysis of HNP-1 and HNP-2 showed that their effect was chemotactic rather than chemokinetic. HNP-3, which differs from HNP-1 only by substitution of aspartate for the amino terminal alanine, was not able to stimulate T-cell chemotaxis. It has been proposed that HNP-3 is a precursor of HNP-2 (24) and proteolytic removal of the amino terminal aspartate residue converts the inactive HNP-3 into chemotactically active HNP-2 (24). While serum proteins have been reported to inhibit the antimicrobial activity of defensins (24), both HNP-1 and HNP-2 retained in vitro chemotactic activity for human T cells in the presence of 10% human serum.

Identification of CAP37/Azurocidin as T-cell Chemoattractants. The second major peak of T-cell chemotactic activity (FIG. 1) was also further purified using the same C4 reversed phase HPLC column. In this case T-cell chemotactic activity co-eluted with a major protein peak corresponding to a homogeneous 30 kDa band on Tris-glycine SDS-PAGE (FIG. 3). Amino-terminal sequence analysis identified this protein as CAP37 (cationic antimicrobial protein of molecular mass 37 kDa) also known as azurocidin (Table 1). By amino acid analysis, our preparation of CAP37/azurocidin corresponds well with the known amino acid composition of CAP37/azurocidin. In addition, upon sequence analysis of our preparation we detected no other sequence except CAP37/azurocidin. These facts indicate that our preparation should prefereably be at least 95% pure. CAP37/azurocidin is a previously identified azurophilic granule protein with sequence homology to the serine protease family and has potent oxygen-independent bactericidal activity (25,26). Sequencing of the polypeptide eluting just before CAP37/azurocidin revealed it to be lysozyme which does not induce T-cell chemotaxis. CAP37 was chemotactic from 1.0 to 100 ng/ml which is comparable in molar concentration to the range of defensin activity (FIG. 4). In addition, preparations of purified as well as recombinant human CAP37/azurocidin were equally potent chemoattractants for human T cells.

Figure 5:
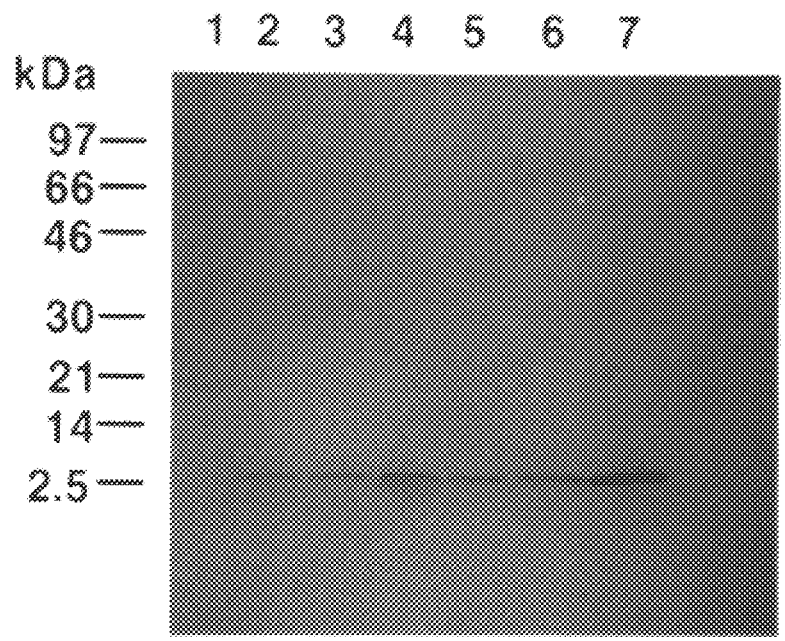
FIG. 5. IL-8, FMLP, and PMA/Ionomycin stimulate the release of defensins from neutrophils in vitro. Human neutrophils were cultured with stimulant for 4 h at 37° after which supernatants were collected and concentrated. The concentrated supernatant was subjected to SDS-PAGE on 4–20% Tris-glycine gel followed by Western blot analysis with anti-defensin rabbit antisera. The stimulants were: Lane 1, media control; Lane 2, IL-8 (50 ng/ml); Lane 3, IL-8 plus cytochalasin B (5 μg/ml); Lane 4, FMLP ($10^{-7}$M); Lane 5, FMLP plus cytochalasin B; Lane 6, PMA (2 ng/ml) plus ionomycin (500 nM). Lane 7, 1 μg of purified defensin preparation.

IL-8 Stimulated Release of Defensins from Neutrophils. Experiments were performed to ensure that defensins would be released into the extracellular environment by appropriate stimuli. Neutrophils exposed to IL-8 were shown to degranulate with the release of lactoferrin and β-glucosidase (20,21). The release of defensins following degranulating stimuli was examined by concentration of the culture supernatants and detection of the defensins released using a Western blot assay (FIG. 5) (27). IL-8 alone was not as effective as PMA/ionomycin or FMLP at degranulation, but the IL-8-stimulated release of granule contents could be increased by the inclusion of cytochalasin B in the assay. TNF-α has also been shown to have a synergistic effect on IL-8-stimulated degranulation (28).

In Vivo Inflammatory Effects of Human Defensins and CAP37/Azurocidin in Mice. BALB/c mice were injected subcutaneously with 1 μg of the defensin or CAP37/azurocidin preparations and after 4 or 24 hrs the injection site was excized and the extent and types of cells infiltrating the site was examined histologically. Within four hours of injection the defensin and CAP37/azurocidin each resulted in infiltration by PMN's and mononuclear cells in the dermis and subcutaneous tissues (Table 2). This is in contrast to a single 1 μg injection of rhIL-8 which produced a marked infiltration of PMN's by four hours with little mononuclear cell infiltration (Taub et al. paper submitted). By 24 hr, 4 hr after a second injection at the same site an even greater infiltration of PMN and mononuclear cells was elicited by defensins as well as CAP37/azurocidin. The latter agent was unique in attracting a considerable number of mast cells along with neutrophils to the injection site by 24 hr. Thus, human defensins and CAP37/azurocidin are capable of inducing considerable local murine neutrophil and mononuclear cell infiltration. Immunohistochemical studies of sites of defensin injection in chimeric huPBL SCID mice were performed to establish whether there were T cells in the infiltrate (22). A single injection of 1 μg of defensins (HNP-1 and HNP-2) within 4 hr resulted in the infiltration by low to modest numbers of human CD3+ T lymphocytes in 4 of 6 mice examined (Table 3). In contrast, the sites of PBS injection in 6 control mice did not contain any human CD3+ T cells. These in vivo results support the in vitro evidence that defensins are T cell chemoattractants.

All literature and patent references cited herein are incorporated by reference as if fully set forth.

TABLE 1

Identification of the T-cell Chemotactic Proteins by Amino-terminal Sequences Analysis

| | |
|---|---|
| HNP-1 | AC<u>YCRIPACIAGERRYGTCIYOGRL</u>WAFCC (SEQ ID NO:1) |
| HNP-2 | <u>CYCRIPACIAGERRYGTCIYOGRL</u>WAFCC (SEQ ID NO:2) |
| HNP-3 | D<u>CYCRIPACIAGERRYGTCIYQGRL</u>WAFCC (SEQ ID NO:3) |
| CAP37/azurocidin | <u>IVGGRKARPRQFPFLASIQNQGRHFC</u>GGALIHARFVMTAA . . . (amino acids 1–40 of SEQ ID NO: 18) |

The complete sequences of HNP-1 and HNP-2 are shown with the amino-terminal sequences obtained from the chemotactic peptides underlined. The presence of cysteine residues was inferred from the absence of detectable amino acid in that cycle. N-terminal sequence of CAP37/azurocidin is shown with the obtained sequence underlined.

TABLE 2

Histological Evaluation of Cellular Infiltration After s.c. Injection of Defensin and Azurocidin in BALB/C Mice

| Animal No. | Dermis | | Subcutaneous Fat | |
|---|---|---|---|---|
| (Treatment) | PMN | MNC | PMN | MNC |
| A) at 4 hr | | | | |
| 21137 (PBS, 1X) | — | — | — | 1F |
| 21138 (PBS, 1X) | — | — | — | 2F |
| 21139 (PBS, 1X) | — | — | — | — |
| 21140 (Defensin, 1X) | — | — | — | 3MF |

TABLE 2-continued

Histological Evaluation of Cellular Infiltration After s.c. Injection of Defensin and Azurocidin in BALB/C Mice

| Animal No. | Dermis | | Subcutaneous Fat | |
|---|---|---|---|---|
| (Treatment) | PMN | MNC | PMN | MNC |
| 21141 (Defensin, 1X) | — | — | — | 2MF |
| 21141 (Defensin, 1X) | — | — | 2MF | 1MF |
| 21143 (Azurocidin, 1X) | 1MF | 1MF | 2MF | 1MF |
| 21144 (Azurocidin, 1X) | — | — | 1MF | 1MF |
| 21145 (Azurocidin, 1X) | 1MF | 1MF | 1MF | 1MF |
| 21146 (Azurocidin, 1X) | — | — | 2MF | 2MF |
| B) at 24 hr | | | | |
| 21153 (PBS, 2X) | 1MF | — | 1F | 1F |
| 21154 (PBS, 2X) | — | — | 2MF | 1F |
| 21155 (PBS, 2X) | — | — | — | — |
| 21156 (Defensin, 2X) | — | — | 3MF | 2MF |
| 21157 (Defensin, 2X) | 1MF | 1MF | 3MF | 3MF |
| 21158 (Defensin, 2X) | 1MF | 1MF | 3MF | 3MF |
| 21159 (Azurocidin, 2X) | — | — | 3MF* | 3MF |
| 21160 (Azurocidin, 2X) | 2F | 1F | 2MF | 2MF |
| 21161 (Azurocidin, 2X) | 2F | — | 2MF* | 2MF |
| 21162 (Azurocidin, 2X) | — | — | 2MF* | 3MF |

Grading:
1 = minimal; 2 = mild; 3 = moderate; 4 = severe; — = no significant lesion; F = focal; MF = multifocal.
Mice received either 1 μg Defensin, 1 μg CAP 37/Azurocidin or PBS s.c. The injection site was then excized and examined histologically on coded slides to determine the extent of leukocyte infiltration.
*The presence of infiltrating mast cells was noted.

TABLE 3

Immunohistological Analysis of Infiltrating Mononuclear Cells in Response to s.c. Injection of Defensin in huPBL-SCID Mice at 4 Hr.

| Animal No. | Treatment | CD3+ Cells |
|---|---|---|
| 21102-1 | PBS (1X) | — |
| 21102-2 | PBS (1X) | — |
| 21103-1 | PBS (1X) | — |
| 21103-2 | PBS (1X) | — |
| 21104-1 | PBS (1X) | — |
| 21104-2 | PBS (1X) | — |
| 21108-1 | Defensin (1X) | 2F* |
| 21108-2 | Defensin (1X) | 2MF* |
| 21109-1 | Defensin (1X) | 2MF* |
| 21109-2 | Defensin (1X) | — |
| 21110-1 | Defensin (1X) | — |

TABLE 3-continued

Immunohistological Analysis of Infiltrating Mononuclear Cells in Response to s.c. Injection of Defensin in huPBL-SCID Mice at 4 Hr.

| Animal No. | Treatment | CD3+ Cells |
|---|---|---|
| 21110-2 | Defensin (1X) | 1F* |

Grading as shown in Table 2
a) Immunohistology was performed on skin sections 4 hr after huPBL injection using antibodies to human CD3. Injection sites were evaluated microscopically without knowledge of the experimental treatment. Immunostaining was graded from minimal (1+) to extensive (4+) based on the intensity and distribution of positive cells.

References

1. Baggiolini, M., Dewald, B. & Moser, B. (1994) *Adv. Immunol.* 55, 97–179.
2. Oppenheim, J. J., Zachariae, C. O. C., Mukaida, N. & Matsushima, K. (1991) *Annu. Rev. Immunol.* 9, 617–648.
3. Bazzoni, F., Cassatella, M. A., Rossi, F., Ceska, M., Dewald, B. & Baggiolini, M. (1991). *J. Exp. Med.* 173, 771–774.
4. Strieter, R. M., Kasahara, K., Allen, R., Showell, H. J., Standiford, T. J., Rolfe, M. W., Becker, F. S., Chensue, S. W. & Kunkel, S. L. (1992) *Am. J. Pathol.* 141, 397–407.
5. Yoshimura, T., Matsushima, K., Tanaka, S., Robinson, E. A., Appella, E., Oppenheim, J. J. & Leonard, E. J. (1987) *Proc. Natl. Acad. Sci. USA* 84, 9233–9237.
6. Walz, A., Peveri, P., Aschauer, H. & Baggiolini, M. (1987) *Biochem. Biophys. Res. Commun.* 149, 755–761.
7. Braun, R. K., Franchini, M., Erard, F., Rihs, S., DeVries, I. J. M., Blaser, K., Hansel, T. T. & Walker, C. (1993) *Eur. J. Immunol.* 23, 956–960.
8. Strieter, R. M., Kunkel, S. L., Showell, H. J., Remick, G. D., Phan, S. H., Ward, P. A. & Marks, R. M. (1989) *Science* 243, 1467–1469.
9. Holmes, W. E., Lee, J., Kuang, W.-J., Rice, G. C. & Wood, W. I. (1991) *Science* 253, 1278–1280.
10. Murphy, P. M. & Tiffany, H. L. (1991) *Science* 253, 1280–1283.
11. Peveri, P., Walz, A., Dewald, B. & Baggiolini, M. (1988) *J. Exp. Med.* 167, 1547–1559.
12. Detmers, P. A., Lo, S. K., Olsen-Egbert, E., Walz, A., Baggiolini, M. & Cohn, Z. A. (1990) *J. Exp. Med.* 171, 1155–1162.
13. Westlin, W. F., Kiely, J.-M. & Gimbrone, Jr. M. A. (1992) *J. Leukocyte Biol.* 52, 43–51.
14. Schroder, J. M., Mrowietz, U., Morita, E. & Christophers, E. (1987) *J. Immunol.* 139, 3474–3483.
15. Willems, J., Joiau, M., Cinque, S. & Van Damme, J. (1989) *Immunology* 67, 540–542.
16. Larsen, C. G., Anderson, A. O., Appella, E., Oppenheim, J. J. & Matsushima, K. (1989) *Science* 243, 1464–1466.
17. Falk, W. R., Goodwin, R. H. & Leonard, E. J. (1980) *J. Immunol. Methods* 33, 239–247.
18. Boyum, A. (1968) *Scand. J. Clin. Lab. Invest.* 21, 77–89.
19. Millard, P. J., Henkart, M. P., Reynolds, C. W. & Henkart, P. A. (1984) *J. Immunol.* 132, 3197–3204.
20. Crouch, S. P. M. & Fletcher, J. (1992) *Infect. Immun.* 60, 4504–4508.
21. Talalay, P., Fishman, W. H. & Huggins, C. (1946) *J. Biol. Chem.* 166, 757–760.
22. Murphy, W. J., Taub, D. D., Anver, M., Conlon, K., Oppenheim, J. J., Kelvin D. J. & Longo, D. L. (1994) *Eur. J. Immunol.* 24, 1823.
23. Schagger, H. & Jagow, G. V. (1987) *Anal. Biochem.* 166, 368–379.
24. Lehrer, R. I., Lichtenstein, A. K. & Ganz, T. (1993) *Annu. Rev. Immunol.* 11, 105–128.
25. Pohl, J., Pereira, H. A., Martin, N. M., & Spitznagel, J. K. (1990) *FEBS Lett.* 272, 200–204.
26. Gabay, J. E., Scott, R. W., Campanelli, D., Griffith, J., Wilde, C., Marra, M. N., Seeger, M. & Nathan, C. F. (1989) *Proc. Natl. Acad. Sci. USA* 86, 5610–5614.
27. Coligan, J. E., Kruisbeck, A. M., Margulies, D. H., Shevach, E. M., and Strober, W. eds. *Current Protocols in Immunology* (1993) Vol. 1, 8.10.
28. Brandt, E., Petersen, F. & Flad, H.-D. (1992) *J. Immunol.* 149, 1356–1364.
29. Lehrer, R. I., Ganz, T. & Selsted, M. E. (1991) *Cell* 64, 229–230.
30. Ganz, T. (1987) *Infect. Immun.* 55, 568–571.
31. Lehrer, R. I., Ganz, T., Szklarek, D. & Selsted, M. E. (1988) *J. Clin. Invest.* 81, 1829–1835.
32. Shafer, W. M., Martin, L. E. & Spitznagel, J. K. (1986) *Infect. Immun.* 53, 651–655.
33. Bangalore, N., Travis, J., Onunka, V. C., Pohl, J. & Shafer, W. M. (1990) *J. Biol. Chem.* 265, 13584–13588.
34. Pereira, H. A., Erdem, I., Pohl, J. & Spitznagel, J. K. (1993) *Proc. Natl. Acad. Sci. USA* 90, 4733–4737.
35. Territo, M. C., Ganz, T., Selsted, M. E. & Lehrer, R. I. (1989) *J. Clin. Invest.* 84, 2017–2020.
36. Pereira, H. C., Schafer, W. M., Pohl, J., Martin, L. E. & Spitznagel, J. K. (1990) *J. Clin. Invest.* 85, 1468–1476.
37. Gallin, J. I. (1988) in Phagocytic cells: Disorders of function in inflammation: Basic principles and clinical correlates, eds. Gallin, J. I., Goldstein, I. M. & Snyderman, R. Raven Press, New York pp. 493–511.
38. Saxena, R. K., Saxena, Q. B. & Adler, W. H. (1982) *Nature* 295, 240–244.
39. Gang, T., Metcalf, J. A., Gallin, J. I., Boxer, L. A. & Lehrer, R. I. (1988) *J. Clin. Invest.* 82, 552–556.
40. Miyata, T., Tokunaga, F., Yoneya, T., Yoshikawa, K., Iwanage, S., Niwa, M., Takao, T. & Shimonishi, Y. (1989) *J. Biochem.* 106, 663–668.
41. Selsted et al. (1984) *Infect. Immun.* 45, 150–154.
42. Ganz et al. (1985) *J. Clin. Invest.* 76, 1427–1435.
43. Almeida et al. (1991) *Biochem. Ciophys. Res. Commun.* 177, 688–695.
44. Zimmer et al. (1992) *PNAS (USA)* 89, 8215–8219.
45. Morgan et al. (1991) *J. Immunol.* 147, 3210–3214.

SEQUENCE LISTING ( 1 ) GENERAL INFORMATION:

( i i i ) NUMBER OF SEQUENCES: 18

( 2 ) INFORMATION FOR SEQ ID NO:1:

( i ) SEQUENCE CHARACTERISTICS:
  ( A ) LENGTH: 30 amino acids
  ( B ) TYPE: amino acid
  ( C ) STRANDEDNESS: single
  ( D ) TOPOLOGY: linear ( i i ) MOLECULE TYPE: protein ( i i i ) HYPOTHETICAL: NO ( x i ) SEQUENCE DESCRIPTION: SEQ ID NO:1:

```
Ala Cys Tyr Cys Arg Ile Pro Ala Cys Ile Ala Gly Glu Arg Arg Tyr
 1               5                  10                      15
Gly Thr Cys Ile Tyr Gln Gly Arg Leu Trp Ala Phe Cys Cys
                20              25                  30
```

( 2 ) INFORMATION FOR SEQ ID NO:2:

( i ) SEQUENCE CHARACTERISTICS:
    ( A ) LENGTH: 29 amino acids
    ( B ) TYPE: amino acid
    ( C ) STRANDEDNESS: single
    ( D ) TOPOLOGY: linear ( i i ) MOLECULE TYPE: protein ( i i i ) HYPOTHETICAL: NO ( x i ) SEQUENCE DESCRIPTION: SEQ ID NO:2:

```
Cys Tyr Cys Arg Ile Pro Ala Cys Ile Ala Gly Glu Arg Arg Tyr Gly
 1               5                  10                      15
Thr Cys Ile Tyr Gln Gly Arg Leu Trp Ala Phe Cys Cys
                20              25
```

( 2 ) INFORMATION FOR SEQ ID NO:3:

( i ) SEQUENCE CHARACTERISTICS:
    ( A ) LENGTH: 30 amino acids
    ( B ) TYPE: amino acid
    ( C ) STRANDEDNESS: single
    ( D ) TOPOLOGY: linear ( i i ) MOLECULE TYPE: protein ( i i i ) HYPOTHETICAL: NO ( x i ) SEQUENCE DESCRIPTION: SEQ ID NO:3:

```
Asp Cys Tyr Cys Arg Ile Pro Ala Cys Ile Ala Gly Glu Arg Arg Tyr
 1               5                  10                      15
Gly Thr Cys Ile Tyr Gln Gly Arg Leu Trp Ala Phe Cys Cys
                20              25                  30
```

( 2 ) INFORMATION FOR SEQ ID NO:4:

( i ) SEQUENCE CHARACTERISTICS:
    ( A ) LENGTH: 33 amino acids
    ( B ) TYPE: amino acid
    ( C ) STRANDEDNESS: single
    ( D ) TOPOLOGY: linear ( i i ) MOLECULE TYPE: protein ( i i i ) HYPOTHETICAL: NO ( x i ) SEQUENCE DESCRIPTION: SEQ ID NO:4:

```
Tyr Cys Ser Cys Arg Leu Val Phe Cys Arg Arg Thr Glu Leu Arg Val
 1               5                  10                      15
Gly Asn Cys Leu Ile Gly Gly Val Ser Phe Thr Tyr Cys Cys Thr Arg
```

Val (2) INFORMATION FOR SEQ ID NO:5:

(i) SEQUENCE CHARACTERISTICS:
        (A) LENGTH: 32 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:5:

```
Ala Thr Cys Tyr Cys Arg Thr Gly Arg Cys Ala Thr Arg Glu Ser Leu
 1               5                  10                  15
Ser Gly Val Cys Glu Ile Ser Gly Arg Leu Tyr Arg Leu Cys Cys Arg
            20                  25                  30
```

(2) INFORMATION FOR SEQ ID NO:6:

(i) SEQUENCE CHARACTERISTICS:
        (A) LENGTH: 30 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:6:

```
Thr Cys His Cys Arg Arg Ser Cys Tyr Ser Thr Glu Tyr Ser Tyr Gly
 1               5                  10                  15
Thr Cys Thr Val Met Gly Ile Asn His Arg Phe Cys Cys Leu
            20                  25                  30
```

(2) INFORMATION FOR SEQ ID NO:7:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:7:

```
Val Cys Tyr Cys Arg Ser Arg Gly Cys Lys Gly Arg Glu Arg Met Asn
 1               5                  10                  15
Gly Thr Cys Arg Lys Gly His Leu Leu Tyr Thr Leu Cys Cys Arg
            20                  25                  30
```

(2) INFORMATION FOR SEQ ID NO:8:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: protein (iii) HYPOTHETICAL: NO ( x i ) SEQUENCE DESCRIPTION: SEQ ID NO:8:

Arg Arg Cys Ile Cys Thr Thr Arg Thr Cys Arg Phe Pro Tyr Arg Arg
1               5                       10                      15

Leu Gly Thr Cys Ile Phe Gln Asn Arg Val Tyr Thr Phe Cys Cys
                20                  25                  30

( 2 ) INFORMATION FOR SEQ ID NO:9:

( i ) SEQUENCE CHARACTERISTICS:
        ( A ) LENGTH: 33 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:9:

Val Val Cys Ala Cys Arg Arg Ala Leu Cys Leu Pro Arg Glu Arg Arg
1               5                       10                      15

Ala Gly Phe Cys Arg Ile Arg Gly Arg Ile His Pro Leu Cys Cys Arg
                20                  25                  30

Arg ( 2 ) INFORMATION FOR SEQ ID NO:10:

( i ) SEQUENCE CHARACTERISTICS:
        ( A ) LENGTH: 33 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:10:

Val Val Cys Ala Cys Arg Arg Ala Leu Cys Leu Pro Leu Glu Arg Arg
1               5                       10                      15

Ala Gly Phe Cys Arg Ile Arg Gly Arg Ile His Pro Leu Cys Cys Arg
                20                  25                  30

Arg ( 2 ) INFORMATION FOR SEQ ID NO:11:

( i ) SEQUENCE CHARACTERISTICS:
        ( A ) LENGTH: 34 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:11:

Gly Ile Cys Ala Cys Arg Arg Arg Phe Cys Pro Asn Ser Glu Arg Phe
1               5                       10                      15

Ser Gly Tyr Cys Arg Val Asn Gly Ala Arg Tyr Val Arg Cys Cys Ser
                20                  25                  30

Arg Arg ( 2 ) INFORMATION FOR SEQ ID NO:12:

(i) SEQUENCE CHARACTERISTICS:
  (A) LENGTH: 34 amino acids
  (B) TYPE: amino acid
  (C) STRANDEDNESS: single
  (D) TOPOLOGY: linear (ii) MOLECULE TYPE: protein (iii) HYPOTHETICAL: NO (xi) SEQUENCE DESCRIPTION: SEQ ID NO:12:

Gly Arg Cys Val Cys Arg Lys Gln Leu Leu Cys Ser Tyr Arg Glu Arg
1               5                   10                  15
Arg Ile Gly Asp Cys Lys Ile Arg Gly Val Arg Phe Pro Phe Cys Cys
                20                  25                  30
Pro Arg (2) INFORMATION FOR SEQ ID NO:13:

(i) SEQUENCE CHARACTERISTICS:
    (A) LENGTH: 33 amino acids
    (B) TYPE: amino acid
    (C) STRANDEDNESS: single
    (D) TOPOLOGY: linear (ii) MOLECULE TYPE: protein (iii) HYPOTHETICAL: NO (xi) SEQUENCE DESCRIPTION: SEQ ID NO:13:

Val Ser Cys Thr Cys Arg Arg Phe Ser Cys Gly Phe Gly Glu Arg Ala
1               5                   10                  15
Ser Gly Ser Cys Thr Val Asn Gly Val Arg His Thr Leu Cys Cys Arg
                20                  25                  30
Arg (2) INFORMATION FOR SEQ ID NO:14:

(i) SEQUENCE CHARACTERISTICS:
    (A) LENGTH: 33 amino acids
    (B) TYPE: amino acid
    (C) STRANDEDNESS: single
    (D) TOPOLOGY: linear (ii) MOLECULE TYPE: protein (iii) HYPOTHETICAL: NO (xi) SEQUENCE DESCRIPTION: SEQ ID NO:14:

Val Phe Cys Thr Cys Arg Gly Phe Leu Cys Gly Ser Gly Glu Arg Ala
1               5                   10                  15
Ser Gly Ser Cys Thr Ile Asn Gly Val Arg His Thr Leu Cys Cys Arg
                20                  25                  30
Arg (2) INFORMATION FOR SEQ ID NO:15:

(i) SEQUENCE CHARACTERISTICS:
    (A) LENGTH: 32 amino acids
    (B) TYPE: amino acid
    (C) STRANDEDNESS: single
    (D) TOPOLOGY: linear (ii) MOLECULE TYPE: protein (iii) HYPOTHETICAL: NO (xi) SEQUENCE DESCRIPTION: SEQ ID NO:15:

```
Val Thr Cys Tyr Cys Arg Arg Thr Arg Cys Gly Phe Arg Glu Arg Leu
1               5                   10                  15

Ser Gly Ala Cys Gly Tyr Arg Gly Arg Ile Tyr Arg Leu Cys Cys Arg
            20              25                  30
```

(2) INFORMATION FOR SEQ ID NO:16:

(i) SEQUENCE CHARACTERISTICS:
        (A) LENGTH: 29 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:16:

```
Cys Ser Cys Arg Thr Ser Ser Cys Arg Phe Gly Glu Arg Leu Ser Gly
1               5                   10                  15

Ala Cys Arg Leu Asn Gly Arg Ile Tyr Arg Leu Cys Cys
            20              25
```

(2) INFORMATION FOR SEQ ID NO:17:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:17:

```
Ala Cys Tyr Cys Arg Ile Gly Ala Cys Val Ser Gly Glu Arg Leu Thr
1               5                   10                  15

Gly Ala Cys Gly Leu Asn Gly Arg Ile Tyr Arg Leu Cys Cys Arg
            20              25                  30
```

(2) INFORMATION FOR SEQ ID NO:18:

(i) SEQUENCE CHARACTERISTICS:
        (A) LENGTH: 222 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:18:

```
Ile Val Gly Gly Arg Lys Ala Arg Pro Arg Gln Phe Pro Phe Leu Ala
1               5                   10                  15

Ser Ile Gln Asn Gln Gly Arg His Phe Cys Gly Gly Ala Leu Ile His
            20              25                  30

Ala Arg Phe Val Met Thr Ala Ala Ser Cys Phe Gln Ser Gln Asn Pro
            35              40                  45

Gly Val Ser Thr Val Val Leu Gly Ala Tyr Asp Leu Arg Arg Arg Glu
    50              55                  60

Arg Gln Ser Arg Gln Thr Phe Ser Ile Ser Ser Met Ser Glu Asn Gly
65              70                  75                  80

Tyr Asp Pro Gln Gln Asn Leu Asn Asp Leu Met Leu Leu Gln Leu Asn
```

|   |   |   | | 8 5 |   |   |   | 9 0 |   |   |   |   | 9 5 |   |   |
|---|---|---|---|---|---|---|---|---|---|---|---|---|---|---|---|
| Arg | Glu | Ala | Asn<br>100 | Leu | Thr | Ser | Ser | Val<br>105 | Thr | Ile | Leu | Pro | Leu<br>110 | Pro | Leu |
| Gln | Asn | Ala<br>115 | Thr | Val | Glu | Ala | Gly<br>120 | Thr | Arg | Cys | Gln | Val<br>125 | Ala | Gly | Trp |
| Gly | Ser<br>130 | Gln | Arg | Ser | Gly | Gly<br>135 | Arg | Leu | Ser | Arg | Phe<br>140 | Pro | Arg | Phe | Val |
| Asn<br>145 | Val | Thr | Val | Thr | Pro<br>150 | Glu | Asp | Gln | Cys | Arg<br>155 | Pro | Asn | Asn | Val | Cys<br>160 |
| Thr | Gly | Val | Leu | Thr<br>165 | Arg | Arg | Gly | Gly | Ile<br>170 | Cys | Asn | Gly | Asp | Gly<br>175 | Gly |
| Thr | Pro | Leu | Val<br>180 | Cys | Glu | Gly | Leu | Ala<br>185 | His | Gly | Val | Ala | Ser<br>190 | Phe | Ser |
| Leu | Gly | Pro<br>195 | Cys | Gly | Arg | Gly | Pro<br>200 | Asp | Phe | Phe | Thr | Arg<br>205 | Val | Ala | Leu |
| Phe | Arg<br>210 | Asp | Trp | Ile | Asp | Gly<br>215 | Val | Leu | Asn | Asn | Pro<br>220 | Gly | Pro | | |

What is claimed is:

1. A method for inducing or stimulating T-cell chemotaxis in a subject which would benefit from such induction or stimulation, said method comprising administering to said subject a pharmaceutical composition comprising a therapeutically effective amount of a defensin protein.

2. The method of claim 1 wherein said defensin protein is a human defensin protein.

3. The method of claim 1 wherein said defensin protein comprises an amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16 and SEQ ID NO:17.

4. The method of claim 3 wherein said defensin protein comprises an amino acid sequence selected from the group consisting of SEQ ID NO:1 and SEQ ID NO:2.

5. The method of claim 1 wherein said composition further comprises a pharmaceutically acceptable carrier.

6. The method of claim 1 wherein said composition further comprises a cytokine.

7. The method of claim 1 wherein said subject is a mammal.

* * * * *